United States Patent [19]

Cosentino

[11] 4,285,337
[45] Aug. 25, 1981

[54] SURGICAL ARM-SLING WITH IMPROVED STRAP ADJUSTMENT

[76] Inventor: Salvatore Cosentino, P.O. Box 488, Woodridge, N.Y. 12789

[21] Appl. No.: 63,391

[22] Filed: Aug. 2, 1979

[51] Int. Cl.³ .............................................. A61F 13/00
[52] U.S. Cl. ...................................... 128/133; 128/94
[58] Field of Search ............... 128/82, 87 R, 94, 133; D24/33, 34; 2/44, 45, 247; 224/49, 205, 219, 222; D3/50, 52

[56] References Cited

U.S. PATENT DOCUMENTS

| D. 223,424 | 4/1972 | Glantz et al. | D3/50 |
|---|---|---|---|
| 2,594,809 | 4/1952 | Sanders | 128/94 |
| 2,718,640 | 9/1955 | Suckle | 2/247 |
| 2,750,597 | 6/1956 | Blatt | 2/44 |
| 2,875,754 | 3/1959 | Messer | 128/94 |
| 3,189,073 | 6/1965 | Todd | 224/222 |
| 4,232,664 | 11/1980 | Blatt | 128/94 |

OTHER PUBLICATIONS

Catalog at Montgomery Ward, Fall and Winter, 1978, pp. 419 and 420.

Primary Examiner—Robert W. Michell
Assistant Examiner—J. L. Kruter
Attorney, Agent, or Firm—William Kovensky

[57] ABSTRACT

An arm sling made of denim and of attractive design with an outside utility pocket, having an infinitely adjustable strap length, and permitting repeated opening and closing without disturbing the adjusted strap length.

6 Claims, 5 Drawing Figures

SURGICAL ARM-SLING WITH IMPROVED STRAP ADJUSTMENT

This invention relates to an improved arm sling having all of the advantages of the state-of-the-art of these devices, while also solving certain problems of the prior art and having new advantages.

The invention sling is of a generally pocket or trough like configuration, of quarter oval shape in elevation and open at the top and at one end for the user's arm and hand respectively.

Throughout this description, drawings and claims, the invention will be shown and described for use on a right arm. Of course, use for a left arm also is contemplated, a right hand sling being usable as is. However, it is preferable to manufacture invention slings as rights and lefts so that the physician can examine the arm more easily and so that the pocket shows and is more easily usable.

The closed corner is suitably contoured to rest the wearer's elbow comfortably and to position the arm correctly for healing.

The improved neck strap of the invention has one end secured to the top end of this closed corner, and its other end is free for adjustable attachment to the dual purpose strap connector and snap fixed to the free corner of the inside (user's body side) wall of the sling. In this manner, the strap can be initially adjusted by the physician, and the snap closure can be repeatedly opened and closed without disturbing the neck strap adjusted length. It is necessary to open the sling many times during the healing process, as for washing, sleeping, exercise and medical examination. This feature of independant strap adjustment makes the invention sling easy, time saving and comfortable to use and prevents changes in position of the arm while in the sling to enhance healing. The strap length is infinitely adjustable as opposed to adjustable to only a few certain fixed lengths, as in the case in some of the prior art.

Another related feature with complimentary advantages is the use of elastic material as the strap. The slight give of the elastic material further enhances comfort by absorbing minor shocks, reducing pains and cramps in the neck, and permitting greater freedom of motion which may be required periodically.

Prior art conventional arm slings generally range in appearance from plain to repulsive, depending on the user's tastes. The invention solves this prior art problem by providing an attractive appearance, especially to younger persons. Appearance can have an impact on healing as the user who is displeased by his or her sling is likely to discontinue its use before the healing process is complete, i.e., an ugly sling is much more likely to be discarded long before the doctor authorizes it than would a sling which the user does not mind or might even have fun wearing.

In general, the invention solves these prior art problems and achieves its advantages as to style and appearance by the use of a jeans motif. The sling body is simply sewn from denim, blue or any other color. This has another advantage in that denim is strong and rugged, is easily sewn, and launders well, the fading due to laundering being an added bonus to many young people. If white denim is used, friends of the wearer can sign the sling, as is the well known custom on casts used to set broken bones.

Yet another feature and advantage is the use of standard belting material for the strap, particularly such material having the word "jeans" woven into it artistically as the design. The sling manufacturer can simply buy rolls of such strapping, cut lengths, sew one end to the sling body, and that aspect is done and the overall design impact is enhanced. The manufacturer can also use suitably colored thread in the sewing, i.e., red thread on blue denim, to again increase the design comliness of the sling at no extra cost of the manufacturer.

Yet another feature having both design and utilitarian advantages is the provision of a pocket sewn on the outside (away from the user's body) wall of the sling body. This pocket is preferably of the patch type, is held in place by both stitching and rivets and may also carry a design, such as a heart, or funny words about broken arms, or the like. A pocket on the outside of this sling is extremely handy for the wearer's keys, cigarettes, etc., as they can be reached with the uninjured arm since the wearer may not be able to get at normal pockets or purse easily because of the sling.

Thus, there is provided an arm sling of the character described which is versatile, strong, durable and attractive in use, and economical to manufacture.

The above and other advantages of the invention will be pointed out or will become evident in the following detailed description and claims and in the accompanying drawings, also forming a part of this disclosure, in which FIG. 1 is a perspective view of a sling embodying the invention with an arm shown in phantom to indicate the environment;

Figure 3:
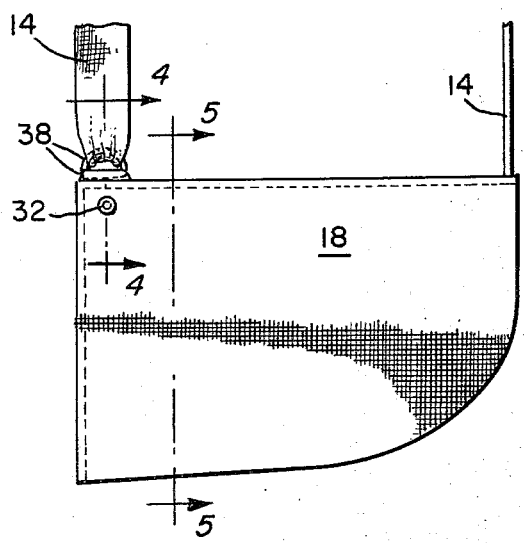
FIG. 3 is a rear (user's body) side elevational view.
Figure 4:
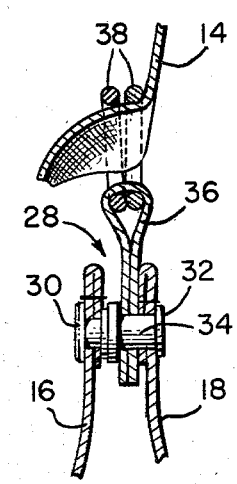
Figure 5:
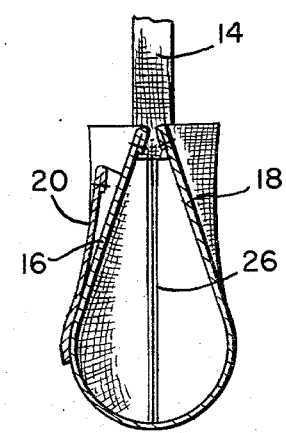

FIGS. 4 and 5 are partial cross-sectional views taken on lines 4—4 and 5—5 respectively of FIG. 3.

Referring now in detail to the drawings, sling 10 comprises a pocket or trough-shaped body 12 and strap 14. Body 12 comprises an outside wall 16 normally positioned away from the user's body, and a similar inside wall 18. A utility pocket 20 is stitched to the outside wall 16 and is also held in place by rivets 22. One end of strap 14 is joined to the body 12 by stitching 24. Stitching 26 (FIG. 4) forms the elbow pocket in the sling joining the ends of the body walls 16 and 18 together and with the strap stitching 24. The strap is long enough to permit the sling to support an arm on the same side shoulder, or to go across the chest and neck to support it from the other side, as is more usual.

The above described features achieve the desirable style and appearance advantages of the invention. The strap 14 preferably is of elastic material, such as belting, has designs or writing, such as the word "jeans" woven into it, the body and pocket are preferably made of denim, and the effect is completed by rivets 22 and all of the stitching described or only shown in the drawing being of a contrasting color to that of the denim, i.e., blue denim and red stitching.

Means are provided to permit the strap length to be adjusted and secured at any one of an infinite number of adjusted lengths, and to permit the sling to be repeatedly opened and closed without changing the adjusted strap length, all for the reasons set forth above. To this end, referring to FIG. 4, a composite fastener assembly 28 is fixed to and positioned between the juxtapositioned free corners of the body walls 16 and 18. Assembly 28 comprises a female snap member 30 conventionally fixed to outside wall 16, and a mating male snap member 32 on the outside wall 18. A short loop 36 is mounted on the shank 34 of the male rivet and carries a pair of rings 38. Loop 36 may also be stitched to wall 18, and preferably the loop is made of the same material as the strap 14 to compliment the overall design motif.

Figure 1:
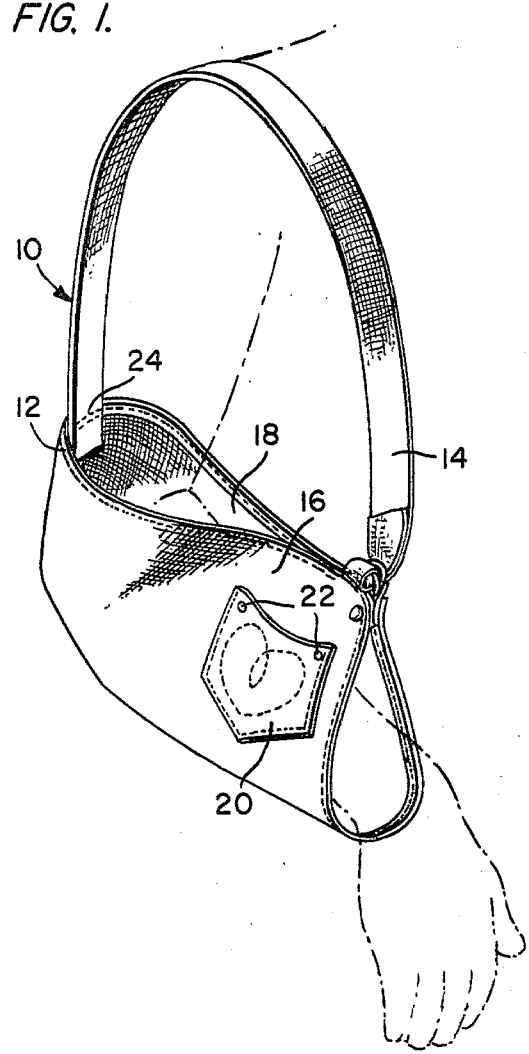
Figure 2:
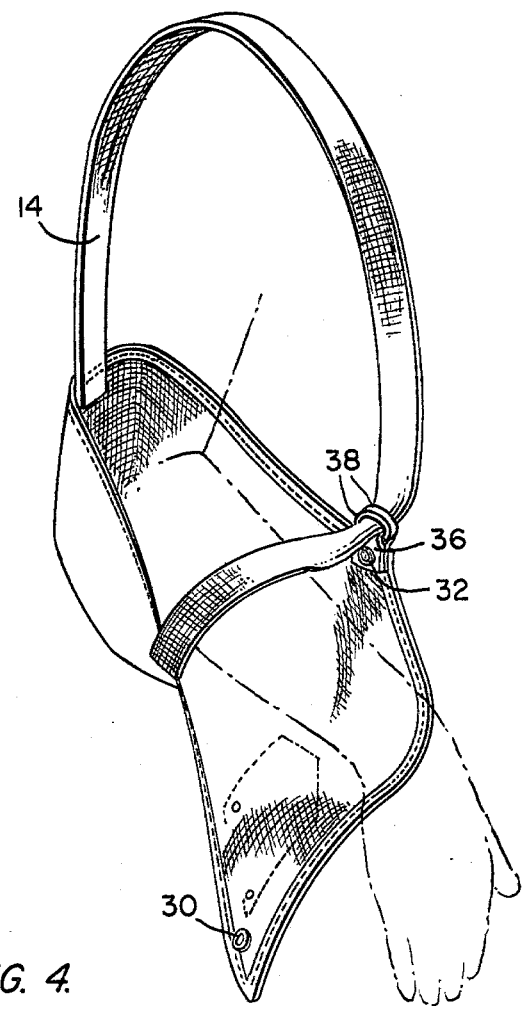
FIG. 2 is a view like FIG. 1 showing the sling snapped open.

Rings 38 are preferably of metal, and they cooperate with the free end of strap 14, just like the straps and rings on knap-sacks, to permit the strap to be easily adjusted to a length desired by the physician, independantly of the snapped open or snapped closed condition of the sling (see FIGS. 2 and 4), and to be secured firmly at that adjusted length (see FIGS. 1 and 3). Once so secured by doubling back on itself as shown in FIG. 1, the snap members 30 and 32 can be repeatedly operated without disturbing the strap length. The rings permit an infinite adjustment of strap length, rather than fixed lengths, as in some prior art slings that use snaps, buttons or the like to control the length of the strap.

While the invention has been described in detail above, it is understood that this detailed description is by way of example only and the protection granted is to be limited only within the spirit of the invention and the scope of the following claims.

I claim:

1. A surgical arm sling comprising a body of trough-like configuration, said body comprising inside and outside walls, means to join said walls to each other at one end of said body to form an elbow pocket, a strap, means to join one end of said strap to said body at said elbow pocket end thereof, composite fastener means comprising ring means to secure said strap at any one of an infinite number of adjusted strap lengths, and said composite fastener means also comprising snap means to permit repeated opening and closing of said sling without disturbing said one adjusted strap length, said strap consisting of elastic material, said snap means comprising a pair of mating snaps secured one to each of said inside and outside body walls at the corners thereof opposite said elbow pocket end, said ring means comprising a pair of rings cooperable with the one end of said strap to infinitely adjust the length of said strap, a loop of the same strap material through said rings to secure said rings to the inside body wall corner, and the ends of said loop being at least partially secured thereto by said snap means at said corner.

2. The sling of claim 1, a utility pocket, and means to fix said utility pocket to the outside surface of said outside body wall.

3. The sling of claim 2, said utility pocket fixing means comprising rivet means.

4. The sling of claim 1, said body consisting essentially of denim.

5. The sling of claim 1, said strap consisting essentially of elastic belting material.

6. The sling of claim 1, said body being made of denim and being stitched together with thread of a contrasting color to the color of the denim, a utility pocket sewn and riveted to the outside of the outside body wall, and said strap being made of elastic material and having design features compatible with the appearance of the body.

* * * * *